United States Patent
Konomura et al.

(10) Patent No.: US 9,715,100 B2
(45) Date of Patent: Jul. 25, 2017

(54) BLADE INSPECTION SYSTEM

(71) Applicant: OLYMPUS CORPORATION, Shibuya-ku, Tokyo (JP)

(72) Inventors: Yutaka Konomura, Tachikawa (JP); Eiichi Kobayashi, Tama (JP); Fumio Hori, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 543 days.

(21) Appl. No.: 14/336,680

(22) Filed: Jul. 21, 2014

(65) Prior Publication Data
US 2015/0035968 A1 Feb. 5, 2015

(30) Foreign Application Priority Data
Aug. 1, 2013 (JP) ................... 2013-160751

(51) Int. Cl.
*G02B 23/24* (2006.01)
*H04N 7/18* (2006.01)
(Continued)

(52) U.S. Cl.
CPC ....... *G02B 23/2484* (2013.01); *G01N 21/954* (2013.01); *G02B 23/2476* (2013.01);
(Continued)

(58) Field of Classification Search
CPC ........................... G01M 15/02; G02B 23/2484
See application file for complete search history.

(56) References Cited

U.S. PATENT DOCUMENTS 3,778,170 A * 12/1973 Howell .............. G02B 23/2476
356/241.4
4,239,451 A * 12/1980 Bouru ................... F01D 11/025
415/173.7
(Continued)

FOREIGN PATENT DOCUMENTS

DE 3707468 A1 9/1987
DE 19513930 A1 9/1996
(Continued)

OTHER PUBLICATIONS

Related U.S. Appl. No. 13/929,564; First Named Inventor: Yutaka Konomura; Title: "Endoscope System"; filed Jun. 27, 2013.
(Continued)

*Primary Examiner* — James Pontius
(74) *Attorney, Agent, or Firm* — Holtz, Holtz & Volek PC

(57) ABSTRACT

Regarding a blade inspection system, each of endo scope guide devices for a borescope has an insertion portion guide tube for guiding an insertion portion and a first fixing portion which is provided on the insertion portion guide tube and fixes the insertion portion guide tube in a corresponding external access port. When the insertion portion is attached into the insertion portion guide tube, lengths of extending portions of the endoscope guide devices are different between the plurality of endoscope guide devices extending from the corresponding external access port so that a position for observing a predetermined portion of a blade by an observation optical system of the insertion portion comes to a position determined in advance for each of the corresponding external access ports.

4 Claims, 9 Drawing Sheets

(51) Int. Cl.
*G01N 21/954* (2006.01)
*F01D 5/00* (2006.01)
*F01D 21/00* (2006.01)

(52) U.S. Cl.
CPC .............. *H04N 7/183* (2013.01); *F01D 5/005* (2013.01); *F01D 21/003* (2013.01); *F05D 2240/12* (2013.01)

(56) References Cited

U.S. PATENT DOCUMENTS

| | | | |
|---|---|---|---|
| 4,659,195 A | | 4/1987 | D'Amelio et al. |
| 4,735,501 A | * | 4/1988 | Ginsburgh ......... G02B 23/2476 356/241.1 |
| 4,784,463 A | | 11/1988 | Miyazaki |
| 5,028,117 A | | 7/1991 | Muhlenkamp-Becker |
| 5,096,292 A | | 3/1992 | Sakamoto et al. |
| 5,102,221 A | * | 4/1992 | Desgranges ........... B23Q 5/027 356/241.1 |
| 5,155,941 A | | 10/1992 | Takahashi et al. |
| 5,335,061 A | | 8/1994 | Yamamoto et al. |
| 5,575,754 A | | 11/1996 | Konomura |
| 6,095,971 A | * | 8/2000 | Takahashi ................ A61B 1/12 600/118 |
| 6,195,119 B1 | * | 2/2001 | Dianna ................. A61B 5/1076 348/65 |
| 7,231,817 B2 | | 6/2007 | Smed et al. |
| 7,250,027 B2 | * | 7/2007 | Barry .................. A61B 1/0056 600/139 |
| 7,340,814 B2 | * | 3/2008 | Bruehwiler ........... B25B 27/143 29/240.5 |
| 7,518,632 B2 | | 4/2009 | Konomura |
| 8,314,834 B2 | | 11/2012 | Konomura |
| 8,714,038 B2 | | 5/2014 | Moran et al. |
| 8,974,372 B2 | * | 3/2015 | Fell ....................... A61B 34/30 600/114 |
| 9,179,824 B2 | * | 11/2015 | Avitsian ............. A61B 1/00135 |
| 2001/0012053 A1 | | 8/2001 | Nakamura |
| 2002/0032371 A1 | * | 3/2002 | Torii .................... A61B 1/0052 600/142 |
| 2002/0161284 A1 | | 10/2002 | Tanaka |
| 2004/0176661 A1 | | 9/2004 | Futatsugi |
| 2005/0014996 A1 | | 1/2005 | Konomura et al. |
| 2005/0148287 A1 | * | 7/2005 | Moeller ................. B24B 19/14 451/6 |
| 2005/0240209 A1 | * | 10/2005 | Hamada ................ A61B 17/02 606/191 |
| 2006/0149126 A1 | | 7/2006 | Ertas et al. |
| 2006/0173243 A1 | | 8/2006 | Watanabe |
| 2006/0276873 A1 | * | 12/2006 | Sato .................... A61B 17/3468 623/1.11 |
| 2007/0171406 A1 | | 7/2007 | Stokes |
| 2008/0262311 A1 | | 10/2008 | Itou et al. |
| 2010/0087708 A1 | | 4/2010 | Chen et al. |
| 2010/0275574 A1 | * | 11/2010 | Salunkhe .............. F01D 21/003 60/39.091 |
| 2012/0098940 A1 | | 4/2012 | Zombo et al. |
| 2012/0101769 A1 | | 4/2012 | Zombo et al. |
| 2012/0184814 A1 | | 7/2012 | Ebata et al. |
| 2013/0008233 A1 | | 1/2013 | Kosugi et al. |
| 2013/0135457 A1 | | 5/2013 | Kell et al. |
| 2013/0158354 A1 | * | 6/2013 | Seo .................... A61B 17/0293 600/114 |
| 2014/0155698 A1 | * | 6/2014 | Seo .................... A61B 17/3423 600/204 |
| 2015/0002841 A1 | | 1/2015 | Kobayashi et al. |
| 2015/0036127 A1 | | 2/2015 | Kobayashi et al. |
| 2016/0192822 A1 | * | 7/2016 | Ofir ..................... A61B 1/00105 600/104 |
| 2016/0338681 A1 | * | 11/2016 | Smith ................... A61B 1/018 |

FOREIGN PATENT DOCUMENTS

| | | |
|---|---|---|
| EP | 1811136 A2 | 7/2007 |
| EP | 2485079 A1 | 8/2012 |
| EP | 2597273 A2 | 5/2013 |
| GB | 2033973 A | 5/1980 |
| JP | 04267213 A | 9/1992 |
| JP | 05297286 A | 11/1993 |
| JP | 2007163723 A | 6/2007 |
| JP | 2011039193 A | 2/2011 |
| WO | 2012054439 A1 | 4/2012 |
| WO | 2013045108 A1 | 4/2013 |

OTHER PUBLICATIONS

Related U.S. Appl. No. 14/336,760; First Named Inventor: Yutaka Konomura; Title: "Blade Inspection Apparatus"; filed Jul. 21, 2014.
Extended European Search Report dated Dec. 16, 2014 issued in counterpart European Application No. 14178313.4.
Japanese Office Action (and English translation thereof) dated Apr. 18, 2017 issued in counterpart Japanese Application No. 2013-160751.

* cited by examiner

BLADE INSPECTION SYSTEM

CROSS REFERENCE TO RELATED APPLICATION

This application claims benefit of Japanese Application No. 2013-160751 filed in Japan on Aug. 1, 2013, the entire contents of which are incorporated herein by this reference.

BACKGROUND OF THE INVENTION

1. Field of the Invention

The present invention relates to a blade inspection system and particularly relates to a blade inspection system for inspecting a blade of an engine.

2. Description of the Related Art

Recently, in inspecting a blade of a jet engine and the like, such a practice that an endoscope is inserted into the jet engine, an inspection image of the blade is obtained, and the blade is inspected is widely performed.

In the blade inspection, an inspector inserts an insertion portion of the endoscope into a plurality of external access ports provided in a casing of the engine, and the inspector advances a distal end portion of the insertion portion to an observation target portion, while he/she watches the inspection image of an inside of the engine displayed on a monitor. That is, the inspector inserts the insertion portion into each of the external access ports, and the inspector inspects presence of a scratch and the like at a predetermined portion of the blade in the engine or over a predetermined inspection range from the predetermined portion, while he/she watches the inspection image displayed on the monitor.

Moreover, as disclosed in Japanese Patent Application Laid-Open Publication No. 2007-163723, a technology in which a fixing tool is attached to the external access port, and the insertion portion of the endoscope is inserted into the engine is proposed. The fixing tool is installed with two pressing plates brought into contact with a wall surface of the jet engine, and the insertion portion of the endoscope device is inserted and fixed to the external access port.

SUMMARY OF THE INVENTION

A blade inspection system of an aspect of the present invention is a blade inspection system for inspecting a plurality of blades periodically disposed on a periphery of a rotating shaft of a rotor of an engine and rotated on the rotating shaft and has an endoscope having an insertion portion in which an observation optical system is provided and a plurality of guide devices attached to external access ports different from each other of the engine in order to guide the insertion portion of the endoscope into the engine. Each of the guide devices has a guide tube for guiding the insertion portion and a first fixing portion which is provided on the guide tube and fixes the guide tube in the corresponding external access port, and a length of an extending portion of the guide device extending from the corresponding external access port is different among the plurality of guide devices so that, when the insertion portion is attached in the guide tube, a position for observing a predetermined portion of the blade by the observation optical system of the insertion portion comes to a position determined in advance for each of the corresponding external access ports.

DETAILED DESCRIPTION OF THE PREFERRED EMBODIMENTS

Figure 1:
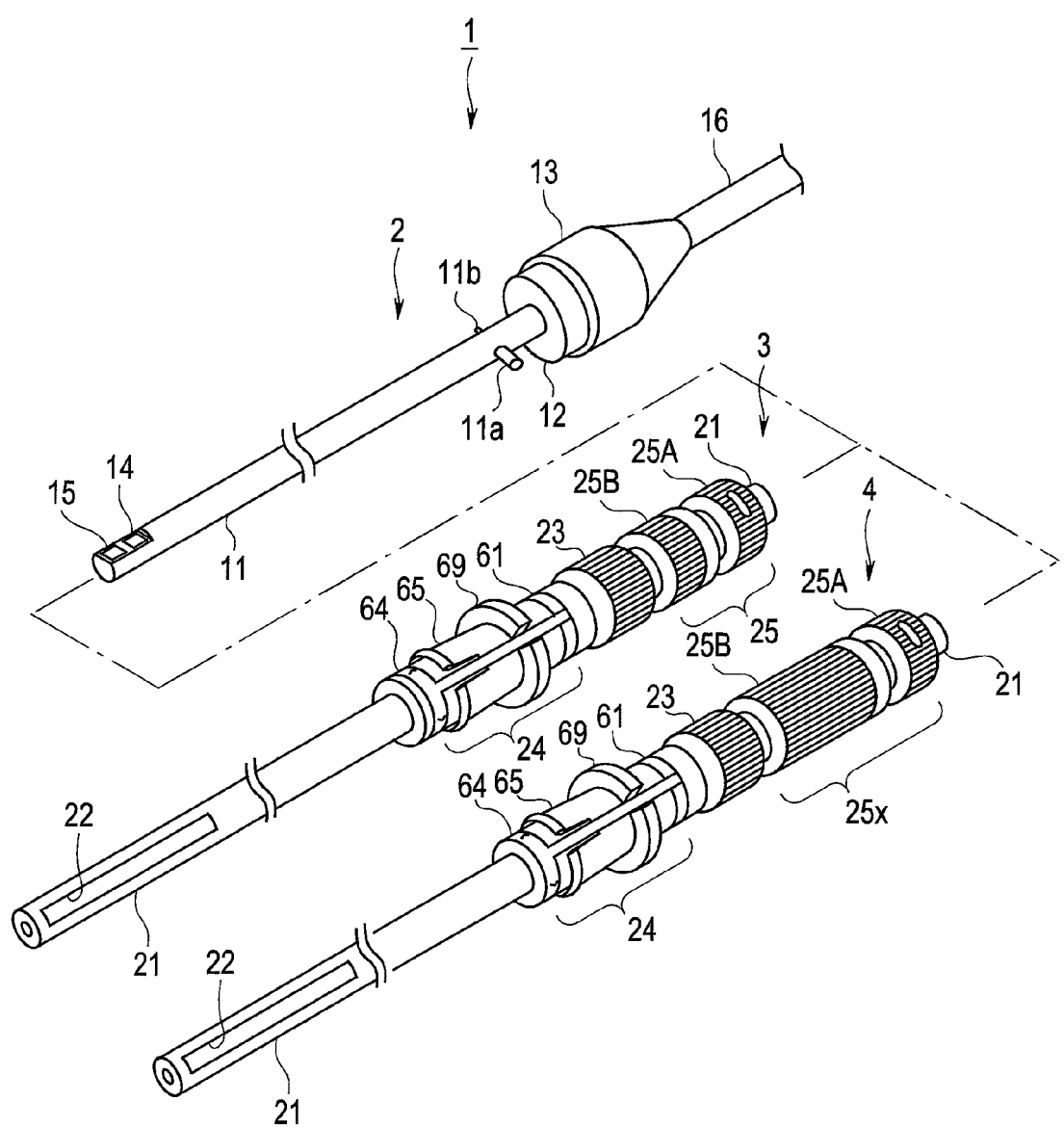
FIG. 1 is a perspective view illustrating an entire configuration of a blade inspection system according to an embodiment of the present invention.

Embodiments of the present invention will be described below by referring to the drawings.

Note that, in the following explanation, the figures based on the embodiments are schematic, and a relationship between a thickness and a width of each portion, a ratio of a thickness among the respective portions and the like are different from actual ones, and even among the figures, those with different relationships of dimensions or different ratios might be included.

System Configuration

First, a blade inspection system of the embodiment of the present invention will be described below on the basis of the drawings.

Figure 2:
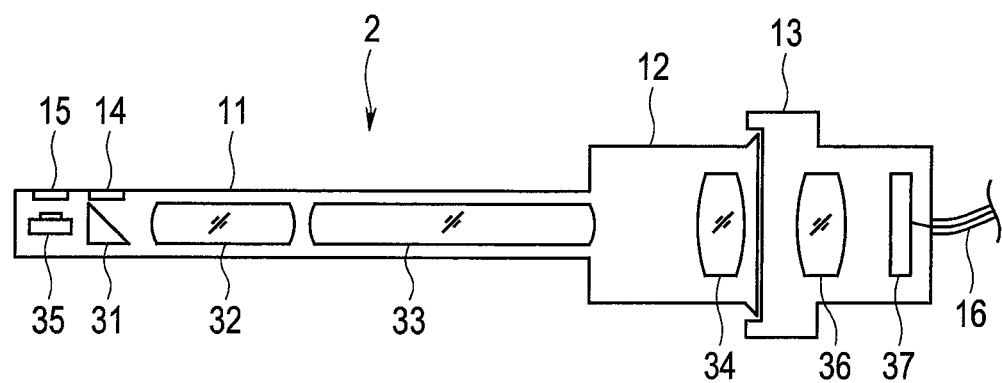
FIG. 2 is a diagram schematically illustrating configurations of a borescope and an image pickup apparatus according to the embodiment of the present invention.
Figure 3:
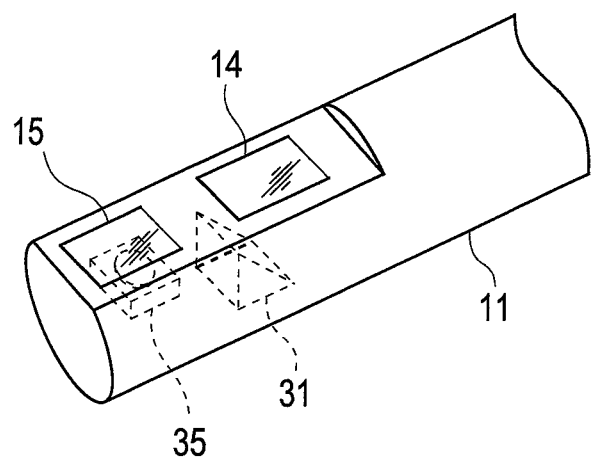
FIG. 3 is a perspective view illustrating a configuration of a distal end portion of an insertion portion of the borescope according to the embodiment of the present invention.

FIG. 1 is a perspective view illustrating an entire configuration of the blade inspection system, FIG. 2 is a diagram schematically illustrating configurations of a borescope and an image pickup apparatus, and FIG. 3 is a perspective view illustrating a configuration of a distal end portion of an insertion portion of the borescope.

A blade inspection system 1 mainly includes, as illustrated in FIG. 1, a borescope 2 as an endoscope and a plurality of endoscope guide devices attached to a jet engine as an object to be inspected which will be described later.

The endoscope guide device to be attached to each of external access ports OAP of each of the engines is determined in advance for each of the external access ports OAP.

That is, each of the endoscope guide devices is a guide device dedicated for the corresponding external access port.

In FIG. 1, only two endoscope guide devices, that is, an endoscope guide device (hereinafter referred to as a first endoscope guide device) 3 and an endoscope guide device (hereinafter referred to as a second endoscope guide device) 4 are illustrated here.

The borescope 2 is a side-view type endoscope and has a cylindrical insertion portion 11 in which an observation window 14 and an illumination window 15 are provided on a side part of a distal end portion and an eyepiece portion 12 disposed at a proximal end portion of the insertion portion 11. Note that, here, a detachable image pickup apparatus 13 is mounted to the eyepiece portion 12 of the borescope 2.

On a proximal end side of the insertion portion 11, two pins 11a and 11b which are projecting portions extending in an outer diameter direction are provided. The two pins 11a and 11b are provided on an outer peripheral portion of the insertion portion 11 axially symmetrically to the insertion portion 11 and projecting to directions opposite to each other. Moreover, an outer diameter of the pin 11a is larger than an outer diameter of the pin 11b.

Inside the borescope 2, observing means and illuminating means are disposed. More specifically, as illustrated in FIGS. 2 and 3, in the insertion portion 11 of the borescope 2, a mirror 31, an objective optical system 32, a relay optical system 33, and an LED 35 as the illuminating means, here, are disposed as an observation optical system. Note that, in the observation window 14 and the illumination window 15, transparent members such as glass are provided.

The mirror 31 is disposed in the distal end portion of the insertion portion 11. The mirror 31 is an optical member which leads light entering the insertion portion 11 from a side surface of the borescope 2 in a direction of the eyepiece portion 12. The objective optical system 32 is disposed on a distal end side of the borescope 2 in the insertion portion 11 and is an optical member for forming a real image of an object.

The LED 35 is an illumination light source emitting an illumination light toward the object and is connected to a wiring cable, not shown, disposed in the insertion portion 11, and a driving power is supplied by the wiring cable.

Note that the power for driving the LED 35 may be configured to be supplied from an outside, or a battery for supplying power may be configured to be provided in the borescope 2. Moreover, the illuminating means is not limited to the LED 35, and the illumination light from an external light source may be configured to be transmitted by a light guide bundle.

In the eyepiece portion 12 of the borescope 2, an eyepiece optical system 34 for visualizing an image transmitted by the relay optical system 33 is provided. In the image pickup apparatus 13 as a camera mounted on the eyepiece portion 12, an image pickup optical system 36 and a solid-state image pickup device 37 are disposed.

The image pickup optical system 36 forms an image of an object visualized by the eyepiece portion 12 of the borescope 2. The solid-state image pickup device 37 picks up an image of the object formed by the image pickup optical system 36.

An image pickup signal which is a video signal photoelectrically converted in the solid-state image pickup device 37 is outputted to a personal computer (PC), not shown, via a signal cable 16. Note that the image pickup signal from the solid-state image pickup device 37 may be configured to be outputted to a video processor or the like via the signal cable 16.

Since the configurations of the borescope 2 and the image pickup apparatus 13 described above are known, detailed explanation of the other configurations will be omitted.

Figure 4:
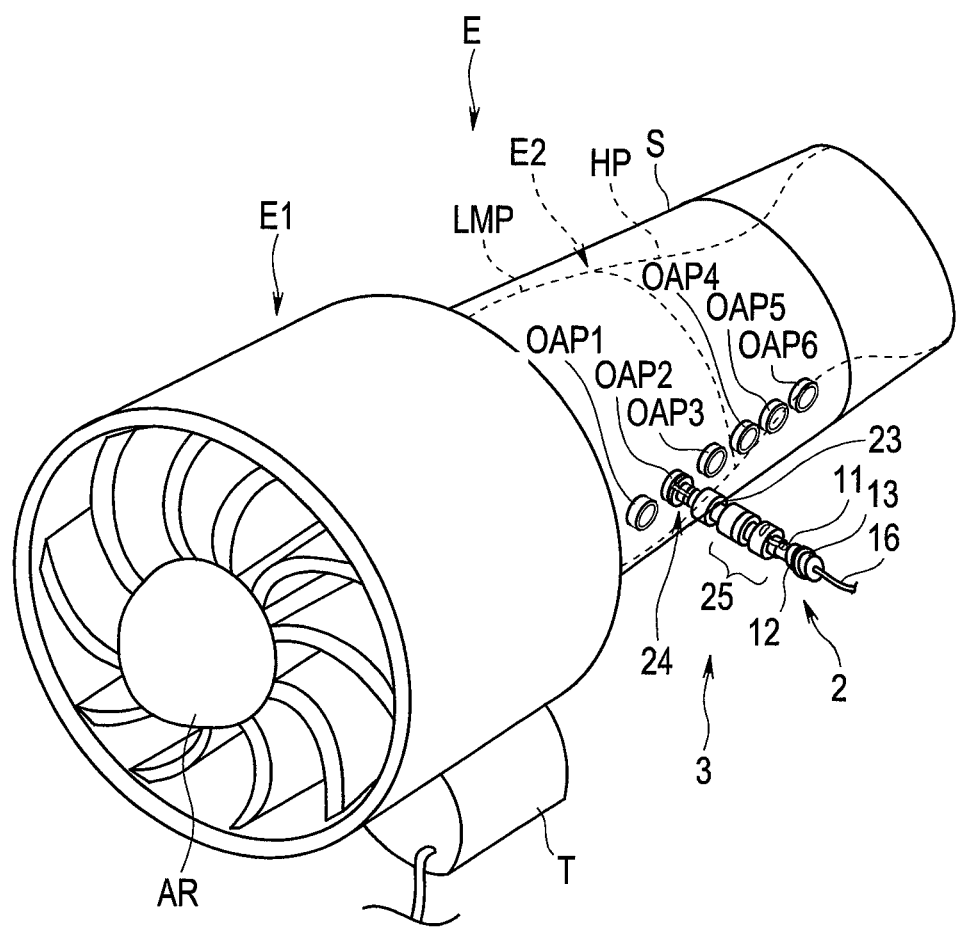
FIG. 4 is a perspective view illustrating a state of an inspection of a jet engine according to the embodiment of the present invention.

FIG. 4 is a perspective view illustrating a state of an inspection of a jet engine. An engine E has, as illustrated in FIG. 4, from an intake side toward an exhaust side, an intake portion E1, a compressor portion E2, a combustion portion, and an exhaust portion (both are not shown in detail).

The compressor portion E2 is covered by a cylindrical skin S which becomes an exterior cover. The compressor portion E2 is an axial-flow type compressor and has a plurality of stages, in which a low-to-medium pressure compressor portion LMP and a high-pressure compressor portion HP are disposed in order from the intake side toward the exhaust side therein.

A plurality of or six external access ports OAP, here, are provided on the skin S. The six external access ports OAP include two external access ports OAP 2 and 3 which become inlets of the first endoscope guide device 3 and the second endoscope guide device 4. To hole portions of these external access ports OAP 2 and 3, the first endoscope guide device 3 and the second endoscope guide device 4 are mounted and fixed. Then, the borescope 2 is inserted into the compressor portion E2 through an insertion portion guide tube 21.

Therefore, the inspector can inspect a plurality of rotor blades RB or stator vanes SV (see FIG. 5) in the compressor portion E2 of the engine E by the first endoscope guide device 3 or the second endoscope guide device 4 and the borescope 2 of the blade inspection system 1.

Moreover, the endoscopic inspection is performed by connecting a turning tool T to the engine E. The turning tool T is a device for rotating a rotating shaft AR, includes a motor and a gearbox, and can rotate the rotating shaft AR through a shaft (not shown).

Then, in the endoscopic inspection, while the plurality of rotor blades which will be described later are rotated around the rotating shaft AR by using the turning tool T, the plurality of rotor blades provided on the rotating shaft AR are photographed by the borescope 2 inserted into the compressor portion E2 and the endoscopic inspection is conducted. Thus, the blade inspection system 1 is a blade inspection system for inspecting the plurality of blades periodically disposed on a periphery of the rotating shaft of the rotor of the engine E and rotated on the rotating shaft. Then, the blade inspection system 1 includes the borescope 2 which is an endoscope having the insertion portion 11 in which the observation optical system is provided and the plurality of guide devices attached to the external access ports OAP which are different from each other of the engine E in order to guide the insertion portion 11 of the borescope 2 into the engine E.

Configuration of Guide Device

Subsequently, a configuration of the endoscope guide device will be described. The two endoscope guide devices 3 and 4 will be mainly described below.

Configuration of First Endoscope Guide Device 3

Figure 5:
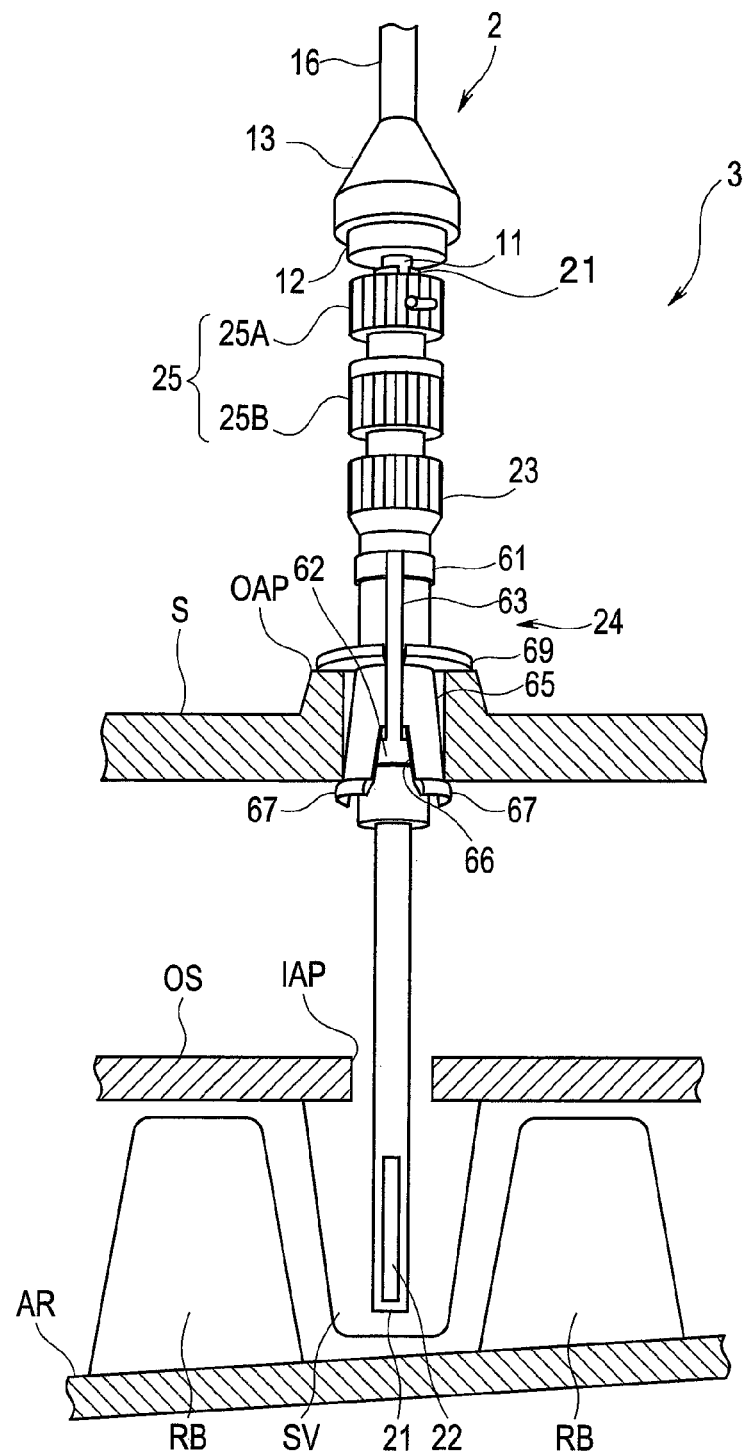
FIG. 5 is a partial sectional view illustrating a state of the inspection of a high-pressure compressor portion according to the embodiment of the present invention.

First, a configuration of the first endoscope guide device 3 will be described. FIG. 5 is a partial sectional view illustrating a state of an inspection of the high-pressure compressor portion. FIG. 5 illustrates a state in which the first endoscope guide device 3 into which the borescope 2 is inserted is inserted in the engine E.

As illustrated in FIGS. 1 and 5, the first endoscope guide device 3 mainly includes the insertion portion guide tube 21, the handle portion 23, the first fixing portion 24, and the second fixing portion 25.

The insertion portion guide tube 21 is capable of insertion/removal of the insertion portion 11 of the borescope 2 and is made of metal, for example, and is a rigid tube with a distal end side closed. On a proximal end side which is an inlet side of the insertion portion guide tube 21, two elongated notch portions 21a and 21b are formed along an axial direction of the insertion portion guide tube 21 (see FIGS. 8 and 9). Widths of the two notch portions 21a and 21b are different from each other, and the width of the notch portion 21a is a width in which the pin 11a provided on the insertion portion 11 of the borescope 2 can enter. The width of the notch portion 21b is a width in which the pin 11b can enter but the pin 11a cannot enter.

The insertion portion guide tube 21 has an observation opening portion 22 as a long hole along a longitudinal direction formed on a side peripheral portion from the distal end side to the middle. The observation opening portion 22 is a window portion for enabling observation of an object by the borescope 2 in a state in which the insertion portion 11 of the borescope 2 is inserted into the insertion portion guide tube 21.

That is, the borescope 2 becomes capable of observing an object by the borescope 2 without a view field shielded by the insertion portion guide tube 21 with the observation window 14 and the illumination window 15 exposed from the observation opening portion 22.

The handle portion 23 is a substantial cylindrical body and is externally inserted into and fixed to the insertion portion guide tube 21.

A configuration of the first fixing portion 24 will be described.

Figure 6:
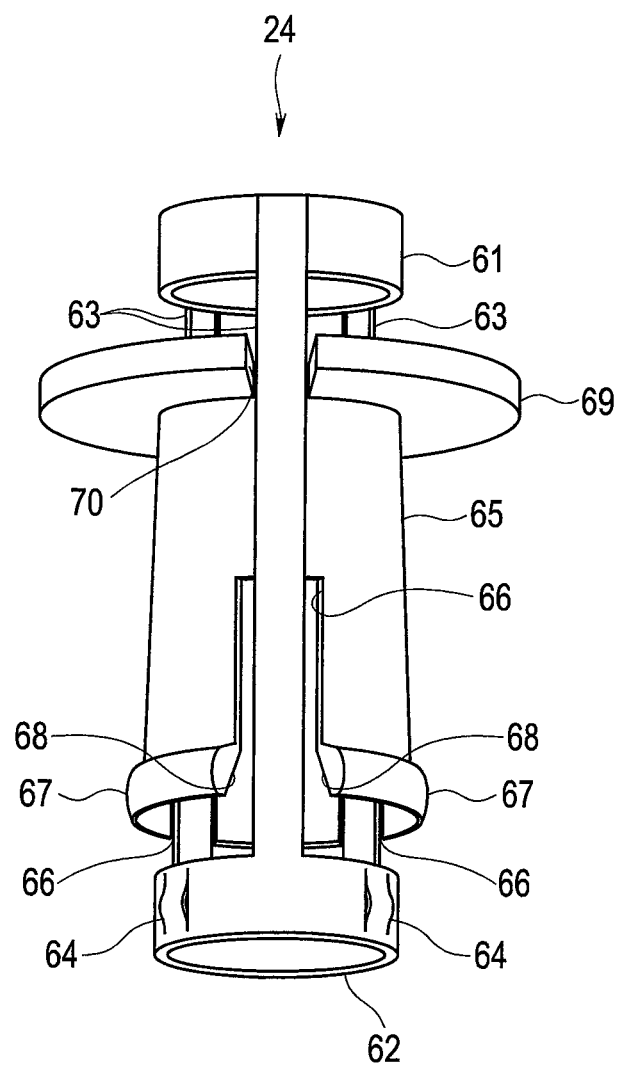
FIG. 6 is a perspective view illustrating a configuration of a first fixing portion 24 of a first endoscope guide device 3 according to the embodiment of the present invention.
Figure 7:
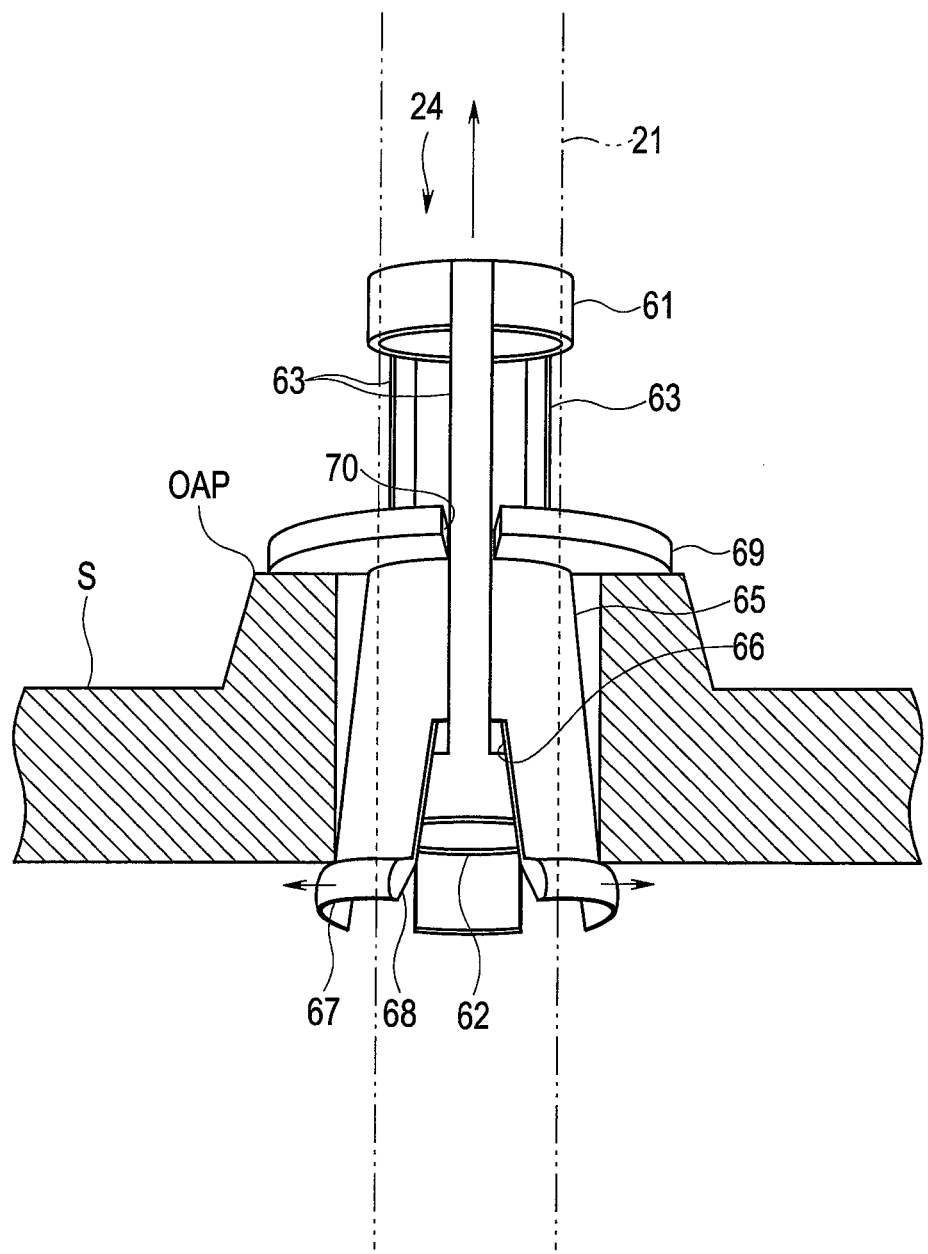
FIG. 7 is a partial sectional view illustrating a state in which the first fixing portion 24 has been inserted into an external access port according to the embodiment of the present invention.

FIGS. 6 and 7 are sectional views illustrating a configuration of the first fixing portion 24 of the first endoscope guide device 3. FIG. 6 is a perspective view illustrating a configuration of the first fixing portion 24, and FIG. 7 is a partial sectional view illustrating a state in which the first fixing portion 24 is inserted into the external access port.

As illustrated in FIG. 6, the first fixing portion 24 includes a first annular portion 61, a second annular portion 62 having an end portion fixed to the first annular portion 61 and having three arm portions 63, here, extending at substantially equal intervals around a periphery, and a fixed cylinder portion 65. On an end portion on the first annular portion 61 side of the fixed cylinder portion 65, an outward flange portion 69 is fixed. The outward flange portion 69 is fixed to the handle portion 23, and the fixed cylinder portion 65 is disposed between the first annular portion 61 and the second annular portion 62 and disposed and fitted on inner sides of the three arm portions 63. Thus, the first annular portion 61 and the second annular portion 62 are capable of advancing/retreating in an axial direction of the handle portion 23 with respect to the fixed cylinder portion 65.

That is, regarding the first fixing portion 24, the first annular portion 61 is connected by the three arm portions 63 extending from the second annular portion 62, and the fixed cylinder portion 65 is disposed inside these three arm portions 63.

Moreover, on the second annular portion 62, three, here, projecting portions 64 (only two of them are shown in FIG. 6) deformed to protrude in an outer diameter direction along two cuts are formed at substantially equal intervals on an outer peripheral portion.

The fixed cylinder portion 65 has three notch portions 66 formed from one end portion which becomes the second annular portion 62 side to a middle portion at positions along the arm portions 63, respectively. Moreover, the fixed cylinder portion 65 has a convex portion 67 projecting in the outer diameter direction formed on an outer peripheral portion on the end portion on the second annular portion 62 side. Then, the fixed cylinder portion 65 has a taper 68 formed on an inner surface side of the convex portion 67 so as to expand in a direction of the one end portion on the second annular portion 62 side.

Moreover, the first fixing portion 24 has the outward flange portion 69 on the end portion on the first annular portion 61 side of the fixed cylinder portion 65 and, as illustrated in FIG. 7, has a configuration such that the outward flange portion 69 and the three convex portions 67 of the fixed cylinder portion 65 sandwich and fix an outer surface and an inner surface around the hole portions of the external access ports OAP 2 provided in the skin S. Note that the outward flange portion 69 of the fixed cylinder portion 65 has a notch portion 70 formed at a position along each of the arm portions 63.

The first fixing portion 24 configured as above is inserted into the hole portion of the external access port OAP 2 when the first fixing portion 24 is to be fixed to the external access port OAP 2 of the skin S, and the outward flange portion 69 of the fixed cylinder portion 65 is made to abut on the outer surface around the hole portion of the external access port OAP 2.

Then, when the inspector pulls up the first annular portion 61, the second annular portion 62 slides with the three arm portions 63 and enters the fixed cylinder portion 65, and as illustrated in FIG. 7, diameters of three end piece portions divided by the three notch portions 66 are expanded in the outer diameter direction.

That is, the first fixing portion 24 is fixed to the external access port OAP 2 such that the outward flange portion 69 of the fixed cylinder portion 65 is made to abut on the outer surface around the hole portion of the external access port OAP 2, the convex portions 67 formed on the three end piece portions expanded in their diameters of the fixed cylinder portion 65 are caught by the inner surface around the hole portion of the external access port OAP 2, and a thickness direction of the skin S is sandwiched by the outward flange portions 69 and the three convex portions 67.

Note that a direction of the first endoscope guide device 3 around the shaft with respect to the external access port OAP 2 is adjusted to a predetermined direction when the first endoscope guide device 3 is attached to the external access port OAP 2. For example, positions (that is, directions) of the first fixing portion 24 and the external access port OAP 2 around an axis of the first endoscope guide device 3 are matched by providing an index mark on each of the fixing portion 24 and the external access port OAP 2 and by matching the two index marks with each other.

As described above, by fixing the first endoscope guide device 3 to the external access port OAP 2 of the skin S by the above described first fixing portion 24, an axis of the insertion portion guide tube 21 can be prevented from shifting or moving.

Subsequently, a configuration of the second fixing portion 25 will be described.

Figure 8:
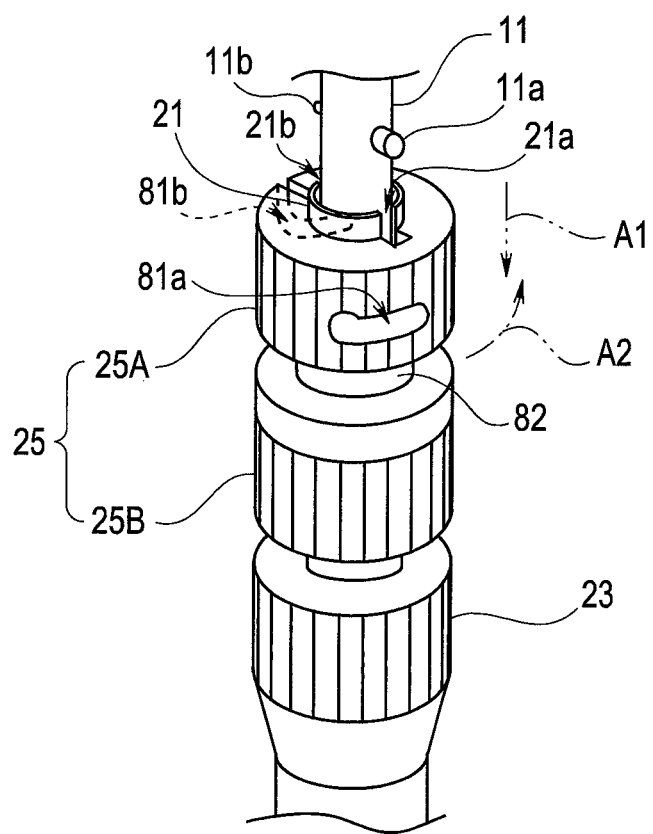
FIG. 8 is a perspective view of portions of a second fixing portion 25 and a handle portion 23 of the first endoscope guide device 3 according to the embodiment of the present invention.
Figure 9:
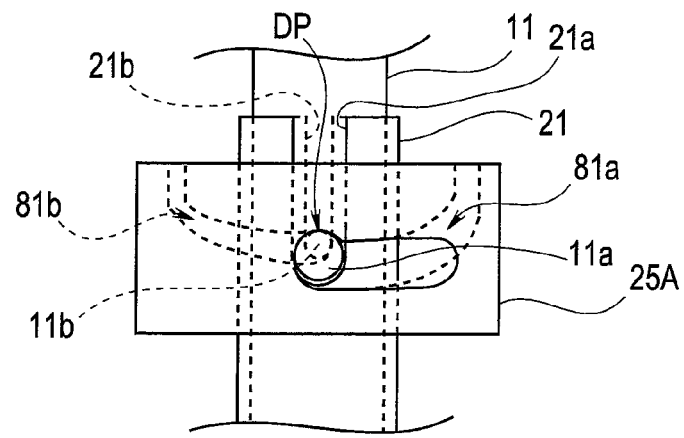
FIG. 9 is a side view of a cam ring 25A of the second fixing portion 25 according to the embodiment of the present invention.
Figure 10:
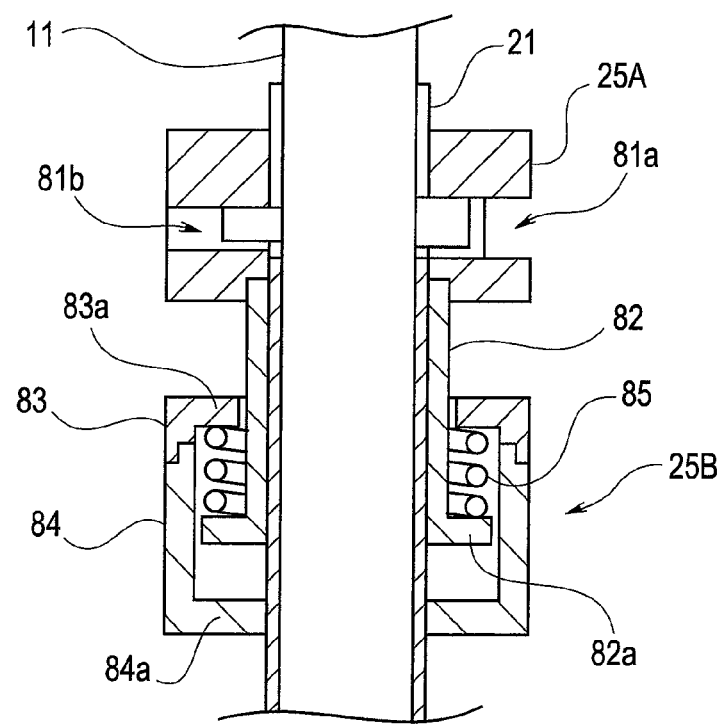
FIG. 10 is a sectional view of the cam ring 25A and a fixed ring 25B of the second fixing portion 25 according to the embodiment of the present invention.

FIG. 8 is a perspective view of parts of the second fixing portion 25 and the handle portion 23 of the first endoscope guide device 3. FIG. 9 is a side view of the cam ring 25A of the second fixing portion 25. FIG. 10 is a sectional view of the cam ring 25A and the fixed ring 25B of the second fixing portion 25.

The second fixing portion 25 is configured by having the cam ring 25A and the fixed ring 25B. The cam ring 25A has a columnar shape and has two cam grooves 81a and 81b formed from an upper surface side toward a side surface. The cam groove 81a is a groove into which the pin 11a as a cam follower enters, and the cam groove 81b is a groove into which the pin 11b as a cam follower enters.

Each of the cam grooves 81a and 81b is formed so as to go from an upper surface toward a lower surface of the cam ring 25A and gently toward a circumferential direction from the middle.

Thus, when the inspector inserts the insertion portion 11 into the insertion portion guide tube 21 of the first endoscope guide device 3, the inspector inserts and fits the pins 11a and 11b in the notch portions 21a and 21b of the insertion portion guide tube 21, respectively. Then, the inspector inserts the pins 11a and 11b in the cam grooves 81a and 81b along the axial direction along a direction indicated by a dotted arrow A1 in FIG. 8 and after that, rotates the cam ring 25A in a direction indicated by a dotted arrow A2 and can advance the pins 11a and 11b along the cam grooves 81a and 81b.

By means of a drop portion DP (see FIG. 9) located at a position where each of the pins 11a and 11b abuts on an abutting portion which is an end surface of each of the cam grooves 81a and 81b, a rotational movement amount around the axis of the insertion portion 11 with respect to the insertion portion guide tube 21 is restricted, and a position around the axis of the borescope 2 with respect to the endoscope guide device 3 is determined.

That is, each of the pins 11a and 11b and each of the cam grooves 81a and 81b are provided on the insertion portion guide tube 21 and constitute a rotational movement amount restricting mechanism portion for restricting the rotational movement amount of the insertion portion 11 around the axis of the insertion portion guide tube 21.

Moreover, as illustrated in FIG. 10, a cylindrical cam-ring spring bracket member 82 is fixed on a lower surface side of the cam ring 25A. The cam-ring spring bracket member 82 extends to a side of the fixed ring 25B and has an outward flange portion 82a at an extended distal end portion.

The cylindrical fixed ring 25B is provided so as to cover the outward flange portion 82a. The fixed ring 25B is composed of two cylindrical bodies 83 and 84. The cylindrical body 83 which is a spring presser has an inward flange portion 83a on a side of the cam ring 25A. The cylindrical body 84 has an inward flange portion 84a on a side of a rotary handle 44. The cylindrical body 83 is fixed to the cylindrical body 84 by an adhesive or the like.

Moreover, the inward flange portion 84a of the cylindrical body 84 is fixed to an outer peripheral surface of the insertion portion guide tube 21 by an adhesive or the like on an inner peripheral surface in contact with the insertion portion guide tube 21.

In an internal space of the fixed ring 25B and between the inward flange portion 83a of the cylindrical body 83 and the outward flange portion 82a of the cam-ring spring bracket member 82, a spring 85 as an elastic member is externally inserted into the cam-ring spring bracket member 82.

As described above, the rotational movement direction and the rotational movement amount around the axis of the borescope 2 with respect to the endoscope guide device 3 are determined by the shapes and the abutting positions of the cam grooves 81a and 81b in which the pins 11a and 11b move, respectively.

Then, in the fixed ring 25B fixed to the insertion portion guide tube 21, the spring 85 is included. One end of the spring 85 is brought into contact with the inward flange portion 83a which is a spring presser, while the other end of the spring 85 is brought into contact with the outward flange portion 82a which is the cam-ring spring bracket, and the spring 85 is disposed so as to be pressed by the outward flange portion 82a and the inward flange portion 83a.

Moreover, the cam-ring spring bracket member 82 is fixed to the cam ring 25A. The pins 11a and 11b are configured so as to be able to move in the axial direction and the circumferential direction along the cam grooves 81a and 81b provided on the cam ring 25A, respectively. Thus, when the pins 11a and 11b are engaged with the cam grooves 81a and 81b, the cam ring 25A is rotatable with respect to the insertion portion guide tube 21 and is also pressed downward which is the handle portion 23 side along the axial direction.

When the insertion portion 11 of the borescope 2 is inserted into the insertion portion guide tube 21, a notch into which the thick pin 11a can enter is the single notch 21a only, and thus, the position around the axis of the borescope 2 becomes a predetermined position, and the position around the axis of the insertion portion 11 with respect to the insertion portion guide tube 21 is determined uniquely, and the insertion portion 11 can be inserted into the insertion portion guide tube 21.

After the insertion, by rotating the cam ring 25A, the pins 11a and 11b move in the circumferential direction along the cam grooves 81a and 81b, respectively, and the two pins 11a and 11b enter the drop portion DP (see FIG. 9) on the deepest side of the cam groove, and the rotational movement of the cam ring 25A is restricted. As a result, the position in the axial direction and around the axis of the insertion portion. 11 with respect to the first endoscope guide device 3 is fixed.

As described above, each of the endoscope guide devices includes the insertion portion guide tube 21 which is a guide tube for guiding the insertion portion 11, the first fixing portion 24 provided on the insertion portion guide tube 21 and fixing the insertion portion guide tube 21 in the corresponding external access port, and the second fixing portion 25 for fixing the insertion portion 11 in the axial direction and around the axis of the insertion portion guide tube 21.

Configuration of Second Endoscope Guide Device 4

A configuration of the second endoscope guide device 4 to be attached to the external access port OAP 3 is substantially the same as the first endoscope guide device 3, but a configuration of the second fixing portion is different.

As described in FIG. 1, a length in the axial direction of a fixing portion 25x of the second endoscope guide device 4 is longer than the length in the axial direction of the second fixing portion 25 of the first endoscope guide device 3. That is because a distance from the skin S of the casing to a predetermined portion to be observed of the blade is different between the external access ports OAP 2 and OAP 3 and thus, the difference in the distance is to be absorbed by the length of the second fixing portion 25x.

In the case of the second endoscope guide device 4, too, when the borescope 2 is attached, the position in the axial direction and the position around the axis of the insertion portion 11 with respect to the second endoscope guide device 4 are fixed to predetermined positions, respectively.

In the four endoscope guide devices attached to the other four external access ports OAP in the six external access ports OAP, too, similarly to the second endoscope guide device 4, the length of the second fixing portion is different from each other so that the difference in the distance from the skin S of the casing to the predetermined position of the blade is absorbed by the length of the second fixing portion.

Operation

Subsequently, an operation of the blade inspection system 1 of this embodiment will be described.

Figure 11:
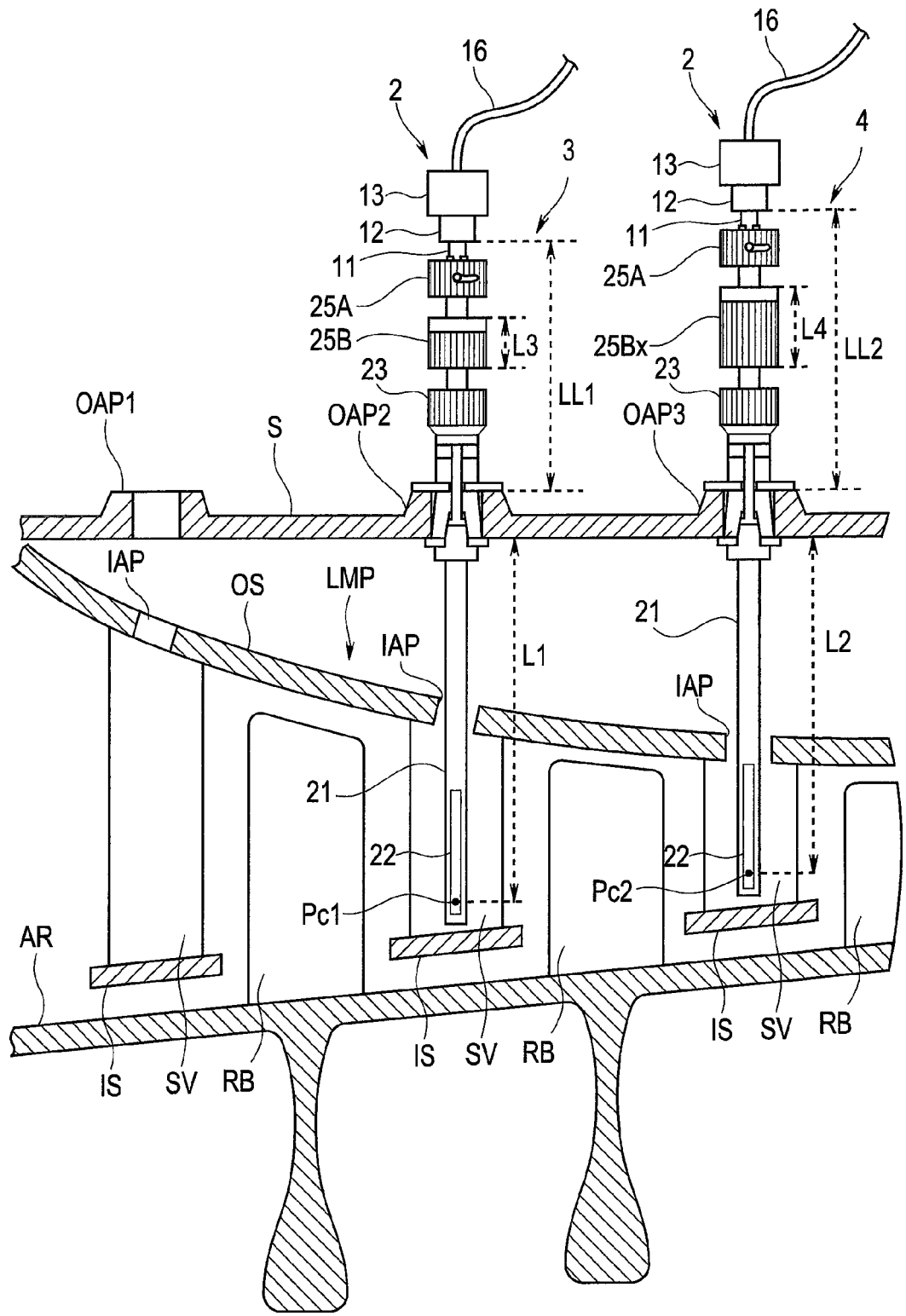
FIG. 11 is a diagram for explaining a state in which the first endoscope guide device 3 and a second endoscope guide device 4 to which a borescope 2 is mounted, respectively, according to the embodiment of the present invention are attached to the corresponding access ports.

FIG. 11 is a diagram for explaining a state in which the first endoscope guide device 3 and the second endoscope guide device 4 to which the borescope 2 is mounted, respectively, are attached to the corresponding access ports, respectively.

The first endoscope guide device 3 is attached to the external access port OAP 2, and the second endoscope guide device 4 is attached to the external access port OAP 3.

As described above, each of the endoscope guide devices is a guide device dedicated for each of the external access ports of each engine. Then, even if the distance from each of the external access ports to the position where a predetermined portion to be observed of the blade as an observation target is observed is different, only by attaching the common borescope 2 to each of the endoscope guide devices, the plurality of endoscope guide devices are configured so that the observation window of the insertion portion of the borescope 2 comes to the position where the predetermined portion to be observed of the blade is observed.

The portion of reference to be observed of the blade is a root portion which is a root part of the blade extending in a radial direction from the rotor, for example. Observation of the blade is performed from such portion of reference in many cases.

Thus, by using the above described plurality of endoscope guide devices, only by inserting and attaching the borescope 2 into the endoscope guide device, the observation window of the insertion portion 11 of the borescope 2 is positioned at a position for observing a portion of reference for the observation, the inspector does not have to adjust the position of the observation window of the insertion portion 11 while he/she watches the inspection image, and the inspector can conduct the inspection of the blade in a short time.

More specific explanation will be given. In the case of an engine structure illustrated in FIG. 11, by means of the borescope 2 inserted from the external access port OAP 2, a reference position Pei of the observation window of the insertion portion 11 for observing the root portion which is a reference portion is a position away from the lower surface of the skin S by a distance L1, by means of the borescope 2 inserted from the external access port OAP 3, a reference position Pc2 of the observation window of the insertion portion 11 for observing the root portion which is a reference portion is a position away from the lower surface of the skin S by a distance L2.

Then, when the common borescopes 2 are inserted into the different endoscope guide devices, respectively, in order that the reference position of the observation window of the borescope 2 matches the reference position of the observation for each of the external access ports OAP, when the common borescope 2 is inserted into each of the endoscope guide devices 3 and 4, the lengths of the endoscope guide devices extending from the first fixing portion 24 to the outside of the engine E are different between the endoscope guide devices 3 and 4.

That is, when the insertion portion 11 is attached into the insertion portion guide tube 21, the lengths of the extending portions of the endoscope guide devices extending from the corresponding external access ports are different among the plurality of the endoscope guide devices so that the position for observing the predetermined portion of the blade by the observation optical system of the insertion portion 11 comes to the position determined in advance for each of the corresponding external access ports. In other words, in order that the lengths of the extending portions of the endoscope guide devices are different among the plurality of endoscope guide devices, the length in the axial direction of the insertion portion guide tube 21 of the second fixing portion is different among the plurality of endoscope guide devices.

In FIG. 11, when the borescope 2 is attached to each of the endoscope guide devices, a length of the portion extending to the outside of the engine E of the endoscope guide device 3 is LL1, and a length of the portion extending to the outside of the engine E of the endoscope guide device 4 is LL2.

That is, when the two pins 11a and 11b are engaged with the cam grooves 81a and 81b of the cam ring 25A of the endoscope guide device 3, respectively, and positioned to the final position of each of the cam grooves, and the two pins 11a and 11b enter the drop portion DP (see FIG. 9), the length LL1 is set so that the reference position for observation at the distal end portion of the insertion portion 11 of the borescope 2 comes to the reference position Pei for observing the predetermined portion (the root portion, for example) of the blade by the borescope 2 inserted from the external access port OAP 2.

Similarly, when the two pins 11a and 11b are engaged with the cam grooves 81a and 81b of the cam ring 25A of the endoscope guide device 4, respectively, and positioned to the final position of each of the cam grooves, and the two pins 11a and 11b enter the drop portion DP (see FIG. 9), the length LL2 is set so that the reference position for observation at the distal end portion of the insertion portion 11 of the borescope 2 comes to the reference position Pc2 for observing the predetermined portion (the root portion, for example) of the blade by the borescope 2 inserted from the external access port OAP 3.

Here, as illustrated in FIG. 11, the lengths LL1 and LL2 are distances from an end surface of the eyepiece portion 12 to the outer surface of the external access port OAP, respectively.

Note that, here, as illustrated in FIG. 11, the length of the insertion portion guide tube 21 extending from the handle portion 23 downward toward the blade is different between the endoscope guide devices 3 and 4 but may be the same. In FIG. 11, due to the presence of an inner shroud IS, a length of the insertion portion guide tube 21 extending downward from the handle portion 23 is different between the endoscope guide devices 3 and 4, but if there are no other structures such as the inner shroud IS in the engine E and if there is no obstruction for the distal end portion of the insertion portion guide tube 21, the length of the insertion portion guide tube 21 extending from the handle portion 23 may be the same among the plurality of endoscope guide devices.

As described above, regarding the insertion portion 11 of the borescope 2, the inspector moves the pins 11a and 11b along the cam grooves 81a and 81b while he/she engages the two pins 11a and 11b with the cam grooves 81a and 81b of the cam ring 25A of the endoscope guide device 3 and attaches the endoscope guide device determined in advance for each of the external access ports OAP of the engine E to the external access ports OAP thereof. Then, the reference position for observation of the borescope 2 in the engine matches the position for observing the portion to be a reference of observation of the blade of each of the external access ports OAP. As a result, the inspector can perform an operation of inserting the insertion portion 11 to a position for picking up an image of the portion to be a reference of observation of the blade in a short time without performing a complicated operation while he/she watches an inspection image displayed on the monitor as before.

The two endoscope guide devices 3 and 4 have been described above, but the same applies to the other endoscope guide devices. That is, each of the endoscope guide devices is a device corresponding to the external access port determined in advance, and whichever endoscope guide device the common borescope is inserted into, the reference position for observation of the borescope 2 in the engine matches the position for observing the portion to be a reference for observation of the blade for each of the external access ports OAP.

As described above, according to the above described embodiment, the blade inspection system in which, after the insertion portion of the endoscope is inserted into the external access port of the engine, the distal end portion of the insertion portion can be located at the position for picking up an image of the portion to be observed of the blade in a short time can be provided.

Particularly, according to the above described embodiment, the common endoscope can be used for the plurality of endoscope guide devices.

Note that, in the above described embodiment, the borescope 2 which is a single common endoscope can be used for the plurality of endoscope guide devices, but a plurality of the borescopes 2 may be used at the same time. That is, it may be so configured that a plurality of the same borescopes are inserted into the plurality of endoscope guide devices, and a plurality of inspection images are obtained at the same time.

If a plurality of such borescopes are used at the same time, since the numbers of blades disposed in the rotor or the like are different among each of the rotor or the like, not only that a plurality of the inspection images can be obtained at the same time, but also a fact that the rotor makes a single rotation can be detected due to the difference in the number of blades.

The invention described in the above described embodiment is not limited to the embodiments and modifications, but in addition to that, various modifications can be put into practice within a range not departing from the gist in a practical stage. Moreover, the above described embodiment includes inventions in various stages, and various inventions can be extracted by appropriate combinations in a plurality of disclosed constituent requirements.

What is claimed is:

1. A blade inspection system for inspecting a plurality of blades periodically disposed on a periphery of a rotating shaft of a rotor of an engine and rotated on the rotating shaft, comprising:
    an endoscope having an insertion portion in which an observation optical system is provided; and
    a plurality of guide devices attached to external access ports different from each other of the engine in order to guide the insertion portion of the endoscope into the engine, wherein
    each of the guide devices has:
    a guide tube for guiding the insertion portion; and
    a first fixing portion which is provided on the guide tube and fixes the guide tube in the corresponding external access port; and
    a length of an extending portion of the guide device extending from the corresponding external access port is different among the plurality of guide devices so that, when the insertion portion is attached in the guide tube, a position for observing a predetermined portion of the blade by the observation optical system of the insertion portion comes to a position determined in advance for each of the corresponding external access ports.

2. The blade inspection system according to claim 1, wherein
    each of the guide devices has a second fixing portion for fixing the insertion portion in an axial direction of the guide tube; and
    in order that the length of the extending portion of the guide device is different among the plurality of guide devices, a length in the axial direction of the guide tube of the second fixing portion is different among the plurality of guide devices.

3. The blade inspection system according to claim 1, wherein
    each of the guide devices has a rotational movement amount restricting mechanism portion which is provided in the guide tube and restricts a rotational movement amount of the insertion portion around an axis of the guide tube.

4. The blade inspection system according to claim 1, wherein
    each of the guide devices has a second fixing portion for fixing the insertion portion in an axial direction of the guide tube and a rotational movement amount restricting mechanism portion which is provided in the guide tube and restricts a rotational movement amount of the insertion portion around an axis of the guide tube; and
    in order that the length of the extending portion of the guide device is different among the plurality of guide devices, a length in the axial direction of the guide tube of the second fixing portion is different among the plurality of guide devices.

* * * * *